United States Patent
Decoster et al.

(10) Patent No.: US 7,186,406 B2
(45) Date of Patent: Mar. 6, 2007

(54) COSMETIC COMPOSITIONS COMPRISING AT LEAST ONE SILICONE COPOLYMER IN AQUEOUS EMULSION AND AT LEAST ONE ASSOCIATIVE THICKENER, AND USES THEREOF

(75) Inventors: Sandrine Decoster, Saint Gratien (FR); Véronique Douin, Paris (FR); Virginie Bailly, Clichy (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/195,021

(22) Filed: Jul. 15, 2002

(65) Prior Publication Data

US 2003/0068291 A1 Apr. 10, 2003

Related U.S. Application Data

(63) Continuation of application No. 09/692,358, filed on Oct. 20, 2000, now abandoned.

(30) Foreign Application Priority Data

Oct. 20, 1999 (FR) .................................. 99 13101

(51) Int. Cl.
*A61Q 5/02* (2006.01)
(52) U.S. Cl. ................. 424/70.12; 424/70.31
(58) Field of Classification Search ............. 424/70.12, 424/70.31
See application file for complete search history.

(56) References Cited

U.S. PATENT DOCUMENTS

| | | |
|---|---|---|
| 2,528,378 A | 10/1950 | Mannheimer |
| 2,781,354 A | 2/1957 | Mannheimer |
| 3,915,921 A | 10/1975 | Schlatzer, Jr. |
| 4,509,949 A | 4/1985 | Huang et al. |
| 5,266,321 A | 11/1993 | Shukuzaki et al. |
| 5,599,533 A | 2/1997 | Stepniewski et al. |
| 5,665,804 A | 9/1997 | Hill et al. |
| 5,989,536 A | 11/1999 | Deckner et al. |
| 6,013,682 A | 1/2000 | Dalle et al. |
| 6,132,707 A * | 10/2000 | Dubief et al. ............. 424/78.08 |
| 6,262,170 B1 | 7/2001 | Kilgour et al. |
| 6,369,117 B1 * | 4/2002 | Dubief et al. ................. 516/55 |
| 6,451,298 B1 | 9/2002 | Decoster et al. |

FOREIGN PATENT DOCUMENTS

| | | | |
|---|---|---|---|
| EP | 0 216 479 | | 4/1987 |
| EP | 0 829 253 | | 3/1998 |
| EP | 0 855 178 | | 7/1998 |
| EP | 0 874 017 | | 10/1998 |
| WO | 99/36045 | * | 7/1999 |

OTHER PUBLICATIONS

M.R. Porter, "Handbook of Surfactants," Blackie & Son Ltd., Glasgow & London, 1991, pp. 116-178.

* cited by examiner

*Primary Examiner*—Margaret G. Moore
(74) *Attorney, Agent, or Firm*—Finnegan Henderson Farabow Garrett & Dunner, L.L.P.

(57) ABSTRACT

Cosmetic compositions comprising, in a cosmetically acceptable medium, at least one aqueous emulsion of at least one silicone copolymer with a dynamic viscosity ranging from $1 \times 10^6$ to $100 \times 10^6$ cP and at least one associative thickener. This combination can give cosmetic properties, such as at least one of smoothness, lightness, and softness, without the phenomenon of regreasing keratin fibers. These compositions can be used for washing and/or conditioning a keratin material, such as the hair or the skin.

87 Claims, No Drawings

COSMETIC COMPOSITIONS COMPRISING AT LEAST ONE SILICONE COPOLYMER IN AQUEOUS EMULSION AND AT LEAST ONE ASSOCIATIVE THICKENER, AND USES THEREOF

This is a Continuation Application of application Ser. No. 09/692,358, filed Oct. 20, 2000 now abandoned.

The present invention relates to novel cosmetic compositions comprising, in a cosmetically acceptable medium, at least one associative thickener and at least one aqueous emulsion of at least one silicone copolymer defined below, with a dynamic viscosity ranging from $1\times10^6$ to $100\times10^6$ cP.

It is well known that hair that has been sensitized (i.e. damaged and/or embrittled) to varying degrees under the action of atmospheric agents or mechanical or chemical treatments, such as dyes, bleaches and/or permanent-waving, can be often difficult to disentangle and to style, and may lack softness.

It has already been recommended to use conditioners, in particular silicones, in compositions for washing or caring for keratin materials such as the hair, in order to facilitate the disentangling of the hair and to give it softness and suppleness. However, the cosmetic advantages mentioned above can be accompanied, on dried hair, by certain cosmetic effects considered undesirable, i.e., lankness of the hairstyle (lack of lightness of the hair), lack of smoothness (hair not uniform from the root to the tip), unpleasant, laden feel, stiffening of the hair and interfiber adhesion which may affect styling to a large extent during repeated use. These drawbacks may be more accentuated in the case of fine hair, which lacks liveliness and body.

In summary, it is found that the current cosmetic compositions comprising silicones are not always entirely satisfactory.

The inventors have now discovered that the combination of an aqueous emulsion of at least one silicone copolymer defined below, with a dynamic viscosity ranging from $1\times10^6$ to $100\times10^6$ cP, with at least one associative thickener makes it possible to overcome at least one of these drawbacks.

Thus, after considerable research conducted in this matter, the inventors have found that by introducing an emulsion of a particular silicone copolymer into compositions, such as hair compositions, containing at least one associative thickener, it is possible to limit, or even eliminate, at least one of the problems generally associated with the use of such compositions, i.e., for example, the lankness (charged feel following repeated applications) and the lack of smoothness and softness of the hair, while at the same time retaining at least one of the other advantageous cosmetic properties which are associated with conditioner-based compositions.

This combination can give cosmetic properties, such as at least one of smoothness, lightness, and softness, without the phenomenon of regreasing keratin fibers.

Moreover, when applied to the skin, for example in the form of a bubble bath or shower gel, the compositions of the invention can provide an improvement in the softness of the skin.

Thus, according to the present invention, cosmetic compositions are now proposed comprising, in a cosmetically acceptable medium, at least one aqueous emulsion of at least one silicone copolymer defined below, wherein said copolymer has a dynamic viscosity ranging from $1\times10^6$ to $100\times10^6$ cP, and at least one associative thickener.

Another subject of the invention relates to the use of at least one aqueous emulsion of at least one silicone copolymer defined below, with a dynamic viscosity ranging from $1\times10^6$ to $100\times10^6$ cP, in, or for the manufacture of, a cosmetic composition comprising at least one associative thickener.

The various subjects of the invention will now be described in detail. All the meanings and definitions of the compounds used in the present invention given below are valid for all the subjects of the invention.

The silicone copolymer generally has a dynamic viscosity, measured at a temperature of about 25° C. and at a shear rate of 0.01 Hz for a stress of 1500 Pa, ranging from $1\times10^6$ cP to $100\times10^6$ cP, such as from $5\times10^6$ cP to $30\times10^6$ cP.

All the dynamic viscosity measurements given in the present patent application were taken at a temperature of about 25° C., on a Carri-Medium CSL2-500 machine.

The at least one silicone copolymer present in the composition according to the invention is in the form of an aqueous emulsion.

The expression "aqueous emulsion" means an emulsion of oil-in-water type in which the at least one silicone copolymer is dispersed, such as in the form of particles or droplets, in the aqueous phase forming the continuous phase of the emulsion. This emulsion can be stabilized with a common emulsifying system.

This silicone emulsion can have a silicone droplet or particle size ranging from 10 nm to 50 μm, such as from 0.3 μm to 20 μm. The particle size is measured by laser granulometry.

The emulsifying system comprises at least one surfactant commonly used in silicone emulsions. The at least one surfactant may be nonionic, cationic, anionic or amphoteric, such as those described below.

The emulsifying system represents, for example, from 0.5% to 10% by weight relative to the total weight of the emulsion.

The at least one silicone copolymer results from the addition reaction, in the presence of a catalyst, of at least:
(a) one polysiloxane of formula (I):

$$R_1-\underset{\underset{R_2}{|}}{\overset{\overset{R_2}{|}}{Si}}-\left[O-\underset{\underset{R_2}{|}}{\overset{\overset{R_2}{|}}{Si}}\right]_n-O-\underset{\underset{R_2}{|}}{\overset{\overset{R_2}{|}}{Si}}-R_1 \qquad (I)$$

in which:
$R_1$, which may be identical or different, are independently chosen from groups that can react by chain addition reaction such as, for example, a hydrogen atom or aliphatic groups comprising an ethylenic unsaturation, such as vinyl, allyl and hexenyl groups;
$R_2$ in formula (I), which may be identical or different, are independently chosen from hydroxyl, alkyl, alkenyl, cycloalkyl, aryl, and alkylaryl groups, and can optionally further comprise functional groups chosen from ethers, amines, carboxyls, hydroxyls, thiols, esters, sulfonates and sulfates; wherein:
the alkyl groups comprise, for example, 1 to 20 carbon atoms; the alkenyl groups comprise, for example, from 2 to 10 carbon atoms; the cycloalkyl groups comprise, for example, 5 or 6 carbon atoms; the aryl groups comprise, for example, phenyl groups; and the alkylaryl groups comprise, for example, from 7 to 20 carbon atoms;
In one embodiment, $R_2$ is chosen from methyl.

n is an integer wherein the polysiloxane of formula (I) has a kinematic viscosity ranging from 1 to $1\times10^6$ mm$^2$/s, for example, n may range from 5 to 5000; and (b) at least one silicone compound comprising at least one and not more than two groups capable of reacting with the groups $R_1$ of the polysiloxane (a), wherein:

at least one of the compounds of type (a) and (b) comprises an aliphatic group, such as a $C_2$–$C_6$ aliphatic group, comprising an ethylenic unsaturation.

The compounds of type (b) can be another polysiloxane of type (a) in which at least one and not more than two groups $R_1$ of the polysiloxane (b) can react with the groups $R_1$ of the polysiloxane (a).

In one embodiment, the at least one silicone copolymer is obtained by addition reaction, in the presence of a hydrosilylation catalyst (for example a platinum catalyst), of at least:

(a) one α,ω-divinylpolydimethylsiloxane, and (b) one α,ω-dihydrogenopolydimethylsiloxane.

The kinematic viscosity is measured, for example, at 25° C. according to ASTM standard 445 Appendix C.

The at least one silicone copolymer according to the invention is essentially non-crosslinked, i.e., not crosslinked to an extent sufficient to be referred to as a crosslinked copolymer.

The synthesis of these silicone emulsions is described for example in patent application EP-A-874 017, the disclosure of which is incorporated by reference herein.

Such emulsions are sold for example under the name DC2-1997 Cationic Emulsion by the company Dow Corning. This emulsion comprises an α,ω-divinyl-dimethicone/α,ω-dihydrogenodimethicone copolymer with a dynamic viscosity of about $15\times10^6$ cP, an emulsifier of cationic type such as cetyltrimethylammonium chloride, a stabilizer such as hydroxyethylcellulose, and water.

The at least one silicone copolymer can be present in a representative amount ranging from 0.05% to 10% by weight relative to the total weight of the composition, such as from 0.1% to 5% by weight relative to the total weight of the composition.

The aqueous emulsion of the at least one silicone copolymer can be present in a representative amount ranging from 0.5% to 15% by weight relative to the total weight of the composition.

As used herein, "associative thickener" refers to an amphiphilic thickener comprising at least one hydrophilic unit and at least one hydrophobic unit.

According to the present invention, the at least one associative thickener may be chosen from associative polymers, wherein said associative polymers may be chosen from:

(i) nonionic amphiphilic polymers comprising at least one fatty chain and at least one hydrophilic unit;

(ii) anionic amphiphilic polymers comprising at least one hydrophilic unit and at least one unit comprising at least one fatty chain;

(iii) cationic amphiphilic polymers comprising at least one hydrophilic unit and at least one unit comprising at least one fatty chain;

(iv) amphoteric amphiphilic polymers comprising at least one hydrophilic unit and at least one unit comprising at least one fatty chain; wherein said at least one fatty chain comprises from 8 to 30 carbon atoms.

In one embodiment, the nonionic amphiphilic polymers comprising at least one fatty chain and at least one hydrophilic unit are chosen from:

(1) Celluloses modified with at least one group comprising at least one fatty chain, such as, for example:

hydroxyethylcelluloses modified with at least one group comprising at least one fatty chain, wherein said at least one fatty chain may comprise at least one group chosen from alkyl groups, arylalkyl groups and alkylaryl groups, wherein said alkyl groups may be chosen from $C_8$–$C_{22}$ alkyl groups. Non-limiting examples of suitable hydroxyethylcelluloses modified with at least one group comprising at least one fatty chain include the product Natrosol Plus Grade 330 CS (comprising $C_{16}$ alkyl groups) sold by the company Aqualon and the product Bermocoll EHM 100 sold by the company Berol Nobel; and celluloses modified with at least one polyalkylene glycol alkylphenyl ether group. Non-limiting examples of celluloses modified with at least one polyalkylene glycol alkylphenyl ether group include the product Amercell Polymer HM-1500 (polyethylene glycol (15) nonylphenyl ether) sold by the company Amerchol;

(2) Hydroxypropyl guars modified with at least one group comprising at least one fatty chain, such as, for example, the product Esaflor HM 22 (comprising $C_{22}$ alkyl groups) sold by the company Lamberti, the product Miracare XC95-3 (comprising $C_{14}$ alkyl groups) and the product RE205-1 (comprising $C_{20}$ alkyl groups) both sold by the company Rhone-Poulenc;

(3) Polyether urethanes comprising at least one fatty chain, such as, for example, polyether urethanes comprising at least one fatty chain comprising at least one group chosen from $C_8$–$C_{30}$ alkyl groups and $C_8$–$C_{30}$ alkenyl groups. Non-limiting examples of said polyether urethanes include the products Dapral T 210, now known as Elfacos T210, and Dapral T 212, now known as Elfacos T212, both sold by the company Akzo and the products Aculyn 44 and Aculyn 46 both sold by the company Rohm & Haas;

(4) Copolymers derived from (i) at least one vinylpyrrolidone monomer and (ii) at least one hydrophobic monomer comprising at least one fatty chain, such as, for example:

the product Antaron V216 and the product Ganex V216 (vinylpyrrolidone/hexadecene copolymer) both sold by the company I.S.P.; and the product Antaron V220 and the product Ganex V220 (vinylpyrrolidone/eicosene copolymer) both sold by the company I.S.P.;

(5) Copolymers derived from (i) at least one monomer chosen from $C_1$–$C_6$ alkyl acrylates and $C_1$–$C_6$ alkyl methacrylates and (ii) at least one amphiphilic monomer comprising at least one fatty chain. A non-limiting example of a suitable copolymer is the oxyethylenated methyl methacrylate/stearyl acrylate copolymer sold by the company Goldschmidt under the name Antil 208; and (6) Copolymers derived from (i) at least one monomer chosen from hydrophilic acrylates and hydrophilic methacrylates and (ii) at least one hydrophobic monomer comprising at least one fatty chain. Non-limiting examples of such copolymers according to the present invention are polyethylene glycol methacrylate/lauryl methacrylate copolymers.

According to the present invention, the anionic amphiphilic polymers comprising at least one hydrophilic unit and at least one unit comprising at least one fatty chain may be chosen from amphiphilic polymers comprising (i) at least one allyl ether unit comprising at least one fatty chain and (ii) at least one hydrophilic unit derived from at least one ethylenic unsaturated anionic monomer. For example, the at least one ethylenic unsaturated anionic monomer may be chosen from vinylcarboxylic acid monomers, such as acrylic acid monomers and methacrylic acids. Further, the at least one allyl ether unit comprising at least one fatty chain may be derived from methacrylic acid monomers of formula (1):

  (1)

wherein:

R' is chosen from H and $CH_3$;

B is chosen from ethyleneoxy groups;

n is an integer ranging from 0 to 100; and

R is chosen from hydrocarbon-based groups chosen from alkyl groups, arylalkyl groups, aryl groups, alkylaryl groups and cycloalkyl groups, wherein said hydrocarbon-based groups comprise from 8 to 30 carbon atoms, such as from 10 to 24 carbon atoms and further such as from 12 to 18 carbon atoms. In one embodiment, R' is H, n is 10 and R is chosen from stearyl groups, that is, $C_{18}$ alkyl groups.

Suitable anionic amphiphilic polymers are described and prepared according to an emulsion polymerization process in patent EP-0 216 479 B2, the disclosure of which is incorporated herein by reference.

The anionic amphiphilic polymers may be chosen from polymers derived from: (i) from 20% to 60% by weight of at least one monomer chosen from acrylic acid and methacrylic acid, (ii) from 5% to 60% by weight of at least one monomer chosen from lower alkyl (meth)acrylates, (iii) from 2% to 50% by weight of at least one monomer chosen from allyl ethers comprising at least one fatty chain of formula (1) above and (iv) from 0% to 1% by weight of at least one crosslinking agent chosen from well-known copolymerizable unsaturated polyethylenic monomers. Non-limiting examples of the at least one crosslinking agent include diallyl phthalate, allyl (meth)acrylate, divinylbenzene, (poly)ethylene glycol dimethacrylate and methylenebisacrylamide.

The anionic amphiphilic polymers may also be chosen from crosslinked terpolymers of (i) methacrylic acid, (ii) ethyl acrylate and (iii) polyethylene glycol (10 EO) stearyl ether (Steareth-10), i.e., Steareth-10 allyl ether, such as the polymers sold by the company Allied Colloids under the names Salcare SC 80 and Salcare SC 90, which are aqueous 30% emulsions of at least one crosslinked terpolymer of methacrylic acid, ethyl acrylate and of steareth-10 allyl ether (40/50/10).

According to the present invention, the anionic amphiphilic polymers may also be chosen from anionic amphiphilic polymers comprising at least one hydrophilic unit (such as at least one unit derived from at least one unsaturated olefinic carboxylic acid) and at least one hydrophobic unit (such as at least one unit derived from at least one $(C_{10}$–$C_{30})$ alkylester of at least one unsaturated carboxylic acid). For example, the at least one unsaturated olefinic carboxylic acid may be chosen from monomers of formula (2):

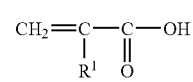  (2)

wherein:

$R^1$ is chosen from H, $CH_3$ and $C_2H_5$. That is, at least one hydrophilic unit may be chosen from acrylic acid units, methacrylic acid units and ethacrylic acid units. Further, the at least one $(C_{10}$–$C_{30})$ alkylester of at least one unsaturated carboxylic acid may be chosen from monomers of formula (3):

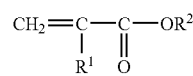  (3)

wherein:

$R^1$ is chosen from H, $CH_3$ and $C_2H_5$; and $R^2$ is chosen from $C_{10}$–$C_{30}$ alkyl groups.

That, is the at least one hydrophobic unit may be chosen from acrylate units, methacrylate units and ethacrylate units. In one embodiment, the at least one hydrophobic unit is chosen from acrylate units ($R^1$=H) and methacrylate units ($R^1$=$CH_3$), wherein $R^2$ is chosen from $C_{12}$–$C_{22}$ alkyl groups.

($C_{10}$–$C_{30}$)Alkyl esters of unsaturated carboxylic acids in accordance with the invention comprise, for example, lauryl acrylate, stearyl acrylate, decyl acrylate, isodecyl acrylate, dodecyl acrylate, methacrylates, lauryl methacrylate, stearyl methacrylate, decyl methacrylate, isodecyl methacrylate and dodecyl methacrylate.

Suitable anionic amphiphilic polymers are disclosed and prepared, for example, according to U.S. Pat. Nos. 3,915,921 and 4,509,949, the disclosures of which are incorporated herein by reference.

According to the present invention, the anionic amphiphilic polymers may also be chosen from:

(i) anionic amphiphilic polymers derived from (a) acrylic acid, (b) at least one ester of formula (3):

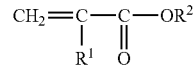  (3)

wherein:

$R^1$ is chosen from H and $CH_3$;

$R^2$ is chosen from alkyl groups comprising from 12 to 22 carbon atoms, and optionally (c) at least one crosslinking agent.

Non-limiting examples of anionic amphiphilic polymers derived from acrylic acid, at least one ester of formula (3) and optionally at least one crosslinking agent include:

polymers derived from 95% to 60% by weight of acrylic acid (hydrophilic unit), 4% to 40% by weight of at least one $C_{10}$–$C_{30}$ alkyl acrylate (hydrophobic unit) and 0% to 6% by weight of at least one crosslinking polymerizable monomer; and polymers formed from 98% to 96% by weight of acrylic acid (hydrophilic unit), 1% to 4% by weight of at least one $C_{10}$–$C_{30}$ alkyl acrylate (hydrophobic unit) and 0.1% to 0.6% by weight of at least one crosslinking polymerizable monomer; and (ii) anionic amphiphilic polymers derived from (a) acrylic acid and (b) lauryl methacylate. A non-limiting example of anionic amphiphilic polymers derived from (a) acrylic acid and (b) lauryl methacylate is polymers derived from 66% by weight of acrylic acid and 34% by weight of lauryl methacrylate.

According to the present invention, the optional crosslinking agent may be chosen from crosslinking polymerizable monomers comprising at least one group of the formula:

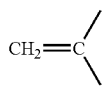

wherein said crosslinking polymerizable monomers further comprise at least one additional polymerizable group wherein if said at least one additional polymerizable group comprises at least one unsaturated bond, then said at least one unsaturated bond is not conjugated. For example, the optional crosslinking agent may be chosen from polyallyl ethers, such as, polyallylsucrose and polyallylpentaerythritol.

The anionic amphiphilic polymers may be chosen from the products sold by the company Goodrich under the trade names Pemulen TR1, Pemulen TR2, Carbopol 1382, and the product sold by the company S.E.P.C. under the name Coatex SX.

Anionic amphiphilic polymers comprising at least one fatty chain may, for example, be chosen from ethoxylated copolymers of methacrylic acid/methyl acrylate/alkyl dimethyl-meta-isopropenylbenzyl-isocyante sold under the name Viscophobe DB 1000 by the company Amerchol.

According to the present invention, the cationic amphiphilic polymers may be chosen from quaternized cellulose derivatives and optionally quaternized polyacrylates comprising at least one amine side chain.

For example, quaternized cellulose derivatives may be chosen from:

quaternized celluloses modified with at least one group comprising at least one fatty chain, wherein said at least one fatty chain may comprise at least one group comprising at least 8 carbon atoms and wherein said at least one group may be chosen from alkyl groups, arylalkyl groups and alkylaryl; and quaternized hydroxyethylcelluloses modified with at least one group comprising at least one fatty chain, wherein said at least one fatty chain may comprise at least one group comprising at least 8 carbon atoms, wherein said at least one group may be chosen from alkyl groups, arylalkyl groups and alkylaryl.

For example, the alkyl groups may comprise from 8 to 30 carbon atoms. Non-limiting examples of aryl groups include phenyl groups, benzyl groups, naphthyl groups and anthryl groups.

The quaternized and non-quaternized polyacrylates comprising at least one amine side chain further comprise at least one hydrophobic group, such as Steareth 20 (polyoxyethylenated(20) stearyl alcohol) and ($C_{10}$–$C_{30}$)alkyl PEG-20 itaconate.

Non-limiting examples of quaternized alkylhydroxyethyl celluloses comprising at least one $C_8$–$C_{30}$ fatty chain include the products Quatrisoft LM 200, Quatrisoft LM-X 529-18-A, Quatrisoft LM-X 529-18B ($C_{12}$alkyl) and Quatrisoft LM-X 529-8 ($C_{18}$alkyl) sold by the company Amerchol and the products Crodacel QM, Crodacel QL ($C_{12}$alkyl) and Crodacel QS ($C_{18}$alkyl) sold by the company Croda.

Non-limiting examples of polyacrylates comprising at least one amine side chain include the polymers 8781-124B, 9492-103 and Structure Plus from the company National Starch.

A non-limiting example of amphoteric amphiphilic polymers comprising at least one fatty chain is copolymers of methacrylamidopropyltrimethylammonium chloride/acrylic acid/$C_{10}$–$C_{30}$ alkyl methacrylate, wherein the alkyl group may, for example, be chosen from stearyl groups.

According to the present invention, the at least one associative thickener has, in solution or in dispersion at a concentration of 1% active material in water, a viscosity, measured using a Rheomat RM 180 rheometer at 25° C., of greater than 0.1 ps, such as greater than 0.2 cp, at a shear rate of 200 s$^{-1}$.

Further, according to the present invention, the at least one associative thickener is present in an amount generally ranging from 0.001% to 20% by weight, such as from 0.01% to 10% by weight and further such as from 0.1% to 3% by weight, relative to the total weight of the final composition.

The compositions of the invention can also comprise at least one surfactant chosen from anionic, amphoteric and nonionic surfactants, which is generally present in an amount ranging from approximately 0.1% to 60% by weight relative to the total weight of the composition, such as from 3% to 40% and further such as from 5% to 30%.

The at least one surfactant chosen from anionic, amphoteric and nonionic surfactants, which are suitable for carrying out the present invention are, for example, the following:

(i) Anionic Surfactant(s):

In the context of the present invention, their nature is not of critical importance.

Representative anionic surfactants include salts (for example alkaline salts, such as sodium salts, ammonium salts, amine salts, amino alcohol salts and magnesium salts) of the following compounds: alkyl sulfates, alkyl ether sulfates, alkylamidoether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates and N-acyltaurates. The alkyl and acyl radicals of all of these various compounds can for example comprise from 8 to 24 carbon atoms, and the aryl radicals can for example be chosen from phenyl and benzyl groups.

For example, anionic surfactants can be chosen from fatty acid salts such as the salts of oleic, ricinoleic, palmitic and stearic acids, coconut oil acid and hydrogenated coconut oil acid and acyl lactylates in which the acyl radical comprises from 8 to 20 carbon atoms. At least one weakly anionic surfactant can also be used, such as alkyl-D-galactosiduronic acids and their salts, as well as polyoxyalkylenated ($C_6$–$C_{24}$) alkyl ether carboxylic acids, polyoxyalkylenated ($C_6$–$C_{24}$) alkylaryl ether carboxylic acids, polyoxyalkylenated ($C_6$–$C_{24}$) alkylamido ether carboxylic acids and their salts, for example, those comprising from 2 to 50 ethylene oxide groups.

As a further example, the anionic surfactant can be at least one salt chosen from alkyl sulfate salts and alkyl ether sulfate salts.

(ii) Nonionic Surfactant(s):

Useful nonionic surfactants include compounds that are well known per se (see for example in this respect "Handbook of Surfactants" by M. R. Porter, published by Blackie & Son (Glasgow and London), 1991, pp. 116–178), the disclosure of which is incorporated by reference herein, and, in the context of the present invention, their nature is not a critical feature. Thus, nonionic surfactants can include polyethoxylated, polypropoxylated and polyglycerolated fatty acids, alkylphenols, α-diols and alcohols having a fatty aliphatic chain comprising, for example, 8 to 18 carbon atoms, it being possible for the number of ethylene oxide and propylene oxide groups to range for example from 2 to 50 and for the number of glycerol groups to range for example from 2 to 30. Mention may also be made of copolymers of ethylene oxide and of propylene oxide, condensates of ethylene oxide and of propylene oxide with fatty alcohols; polyethoxylated fatty amides for example comprising from 2 to 30 mol of ethylene oxide, polyglycerolated fatty amides comprising on average 1 to 5, such as from 1.5 to 4, glycerol groups; polyethoxylated fatty amines for example comprising from 2 to 30 mol of ethylene oxide; oxyethylenated fatty acid esters of sorbitan comprising from 2 to 30 mol of ethylene oxide; fatty acid esters of sucrose, fatty acid esters of polyethylene glycol, alkylpolyglycosides, N-alkylglucamine derivatives, amine oxides such as $(C_{10}-C_{14})$alkylamine oxides and N-acylaminopropylmorpholine oxides. It will be noted that the alkylpolyglycosides are nonionic surfactants that can be suitable in the context of the present invention.

(iii) Amphoteric Surfactant(s):

Representative amphoteric surfactants, whose nature is not a critical feature in the context of the present invention, can be chosen from aliphatic secondary and tertiary amine derivatives in which the aliphatic radical is chosen from linear and branched chain radicals comprising 8 to 22 carbon atoms and comprising at least one water-soluble anionic group (chosen for example from carboxylate, sulfonate, sulfate, phosphate and phosphonate); mention may also be made of $(C_8-C_{20})$alkylbetaines, sulfobetaines, $(C_8-C_{20})$alkylamido$(C_1-C_6)$alkylbetaines and $(C_8-C_{20})$alkylamido$(C_1-C_6)$alkylsulfobetaines.

Representative amine derivatives include the products sold under the name Miranol, as described in U.S. Pat. Nos. 2,528,378 and 2,781,354, the disclosures of which are incorporated by reference herein, and having the structures:

$$R_2—CONHCH_2CH_2—N^+(R_3)(R_4)(CH_2COO—) \quad (2)$$

in which:

$R_2$ is chosen from alkyl radicals derived from an acid $R_2—COOH$ present in hydrolysed coconut oil, heptyl, nonyl and undecyl radicals, $R_3$ is chosen from β-hydroxyethyl groups, and $R_4$ is chosen from carboxymethyl groups; and $$R_5—CONHCH_2CH_2—N(B)(C) \quad (3)$$

in which:

(B) is —$CH_2CH_2OX'$, with X' chosen from a —$CH_2CH_2$—COOH group and a hydrogen atom, (C) is —$(CH_2)_z$—Y', with z=1 or 2, and with Y' chosen from —COOH and —$CH_2$—CHOH—$SO_3H$ radicals, $R_5$ is chosen from alkyl radicals, such as (a) alkyl radicals of an acid $R_5$—COOH present in oils chosen from coconut oil and hydrolysed linseed oil, (b) alkyl radicals, such as $C_7$, $C_9$, $C_{11}$ and $C_{13}$ alkyl radicals, and (c) $C_{17}$ alkyl radicals and the iso forms, and unsaturated $C_{17}$ radicals.

Such representative compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid.

By way of example, mention may be made of the cocoamphodiacetate sold under the trade name Miranol C2M Concentrate by the company Rhône-Poulenc.

In the compositions in accordance with the invention, at least two surfactants of different types can be used. Representative compositions include compositions comprising (a) more than one anionic surfactant, (b) at least one anionic surfactant and at least one amphoteric surfactant, and (c) at least one anionic surfactant and at least one nonionic surfactant. In one embodiment, the composition can comprise at least one anionic surfactant and at least one amphoteric surfactant.

The at least one anionic surfactant used for example, can be chosen from $(C_{12}-C_{14})$alkyl sulfates of sodium, of triethanolamine and of ammonium; $(C_{12}-C_{14})$alkyl ether sulfates of sodium, of triethanolamine and of ammonium, oxyethylenated with 2.2 mol of ethylene oxide; sodium cocoyl isethionate; and sodium $(C_{14}-C_{16})$-α-olefin sulfonate, and used in combination with an amphoteric surfactant chosen from either:

amphoteric surfactants such as the amine derivatives known as disodium cocoamphodipropionate and sodium cocoamphopropionate, sold for example by the company Rhône-Poulenc under the trade name "Miranol C2M Conc®" as an aqueous solution comprising 38% active material, and under the name Miranol C32; or amphoteric surfactants of zwitterionic type, such as alkylbetaines, for example the cocobetaine sold under the name "Dehyton AB 30" as an aqueous solution comprising 32% AM by the company Henkel.

In one embodiment of the invention, the compositions can also comprise at least one cationic surfactant.

Representative at least one cationic surfactants can be chosen from salts of optionally polyoxyalkylenated primary, secondary and tertiary fatty amines; quaternary ammonium salts; imidazoline derivatives; and amine oxides of cationic nature.

The at least one cationic surfactants may, for example, be chosen from:

A) Quaternary ammonium salts of formula (IV) below:

$$\begin{bmatrix} R_1 & R_3 \\ & N & \\ R_2 & R_4 \end{bmatrix}^+ X^- \quad (IV)$$

in which:

the radicals $R_1$, $R_2$, $R_3$, and $R_4$, which may be identical or different, are independently chosen from linear and branched aliphatic radicals comprising from 1 to 30 carbon atoms, and aromatic radicals, such as $C_6-C_{20}$ aromatic radicals (for example, aryl and alkylaryl), wherein the aliphatic radicals can comprise hetero atoms such as, oxygen, nitrogen, sulfur and halogens, and wherein the aliphatic radicals are chosen, for example, from alkyl, alkoxy, polyoxy($C_2$–$C_6$)alkylene, alkylamide, ($C_{12}$–$C_{22}$)alkylamido($C_2$–$C_6$)alkyl, ($C_{12}$–$C_{22}$)alkylacetate and hydroxyalkyl radicals, comprising from 1 to 30 carbon atoms;

$X^-$ is an anion chosen from halides, phosphates, anions derived from organic acids, ($C_2$–$C_6$)alkyl sulfates, alkyl sulfonates, and alkylaryl sulfonates.

The compounds of formula (IV) can be chosen from, for example, (a) compounds comprising at least two fatty aliphatic radicals comprising from 8 to 30 carbon atoms, (b) compounds comprising at least one fatty aliphatic radical comprising from 17 to 30 carbon atoms, and (c) compounds comprising at least one aromatic radical.

B) Quaternary ammonium salts of imidazolinium, such as, for example, the salts of formula (V) below:

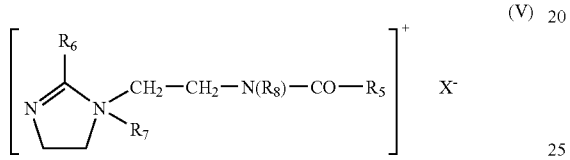

(V)

in which:

$R_5$ is chosen from alkenyl and alkyl radicals comprising from 8 to 30 carbon atoms, for example radicals derived from tallow fatty acid, $R_6$ is chosen from a hydrogen atom, $C_1$–$C_4$ alkyl radicals, and alkenyl and alkyl radicals comprising from 8 to 30 carbon atoms, $R_7$ is chosen from $C_1$–$C_4$ alkyl radicals, $R_8$ is chosen from a hydrogen atom and $C_1$–$C_4$ alkyl radicals, $X^-$ is an anion chosen from halides, phosphates, acetates, lactates, alkyl sulfates, alkyl sulfonates, and alkylaryl sulfonates.

For example, $R_5$ and $R_6$, which may be identical or different, are independently chosen from alkenyl and alkyl radicals comprising from 12 to 21 carbon atoms, for example, radicals derived from tallow fatty acid, $R_7$ is methyl, and $R_8$ is hydrogen.

Such products are, for example, (1) Quaternium-27 (International Cosmetic Ingredient Dictionary and Handbook, hereafter "CTFA", 1997), i.e., "Rewoquat" W75, W75PG, and W90, and (2) Quaternium-83 (CTFA 1997), i.e., "Rewoquat" W75HPG, which are sold by the company Witco.

C) Diquaternary Ammonium Salts of Formula (VI):

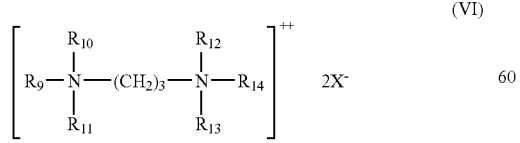

(VI)

in which:

$R_9$ is chosen from aliphatic radicals comprising from 16 to 30 carbon atoms, $R_{10}$, $R_{11}$, $R_{12}$, $R_{13}$ and $R_{14}$, which may be identical or different, are independently chosen from a hydrogen atom and alkyl radicals comprising from 1 to 4 carbon atoms, and $X^-$ is an anion chosen from halides, acetates, phosphates, nitrates and methyl sulfates.

For example, such diquaternary ammonium salts can comprise propane tallow diammonium dichloride.

D) Quaternary ammonium salts comprising at least one ester function. The quaternary ammonium salts comprising at least one ester function that can be used according to the invention are, for example, those of formula (VII) below:

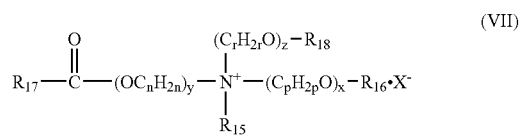

(VII)

in which:

$R_{15}$ is chosen from $C_1$–$C_6$ alkyl radicals and $C_1$–$C_6$ hydroxyalkyl and $C_1$–$C_6$ dihydroxyalkyl radicals;

$R_{16}$ is chosen from:
  acyl groups of the following formula:

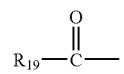

wherein $R_{19}$ is defined below,
  linear and branched, saturated and unsaturated, $C_1$–$C_{22}$ hydrocarbon-based radicals, and
  a hydrogen atom;

$R_{18}$ is chosen from:
  acyl groups of the following formula:

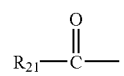

wherein $R_{21}$ is defined below,
  linear and branched, saturated and unsaturated, $C_1$–$C_6$ hydrocarbon-based radicals, and
  a hydrogen atom;

$R_{17}$, $R_{19}$ and $R_{21}$, which may be identical or different, are independently chosen from linear and branched, saturated and unsaturated, $C_7$–$C_{21}$ hydrocarbon-based radicals;

n, p and r, which may be identical or different, are independently integers ranging from 2 to 6;

y is an integer ranging from 1 to 10;

x and z, which may be identical or different, are independently integers ranging from 0 to 10;

$X^-$ is chosen from simple and complex, organic and inorganic anions;

provided that the sum x+y+z is from 1 to 15, and that when x is 0, then $R_{16}$ is chosen from linear and branched, saturated and unsaturated, $C_1$–$C_{22}$ hydrocarbon-based radicals, and that when z is 0, then $R_{18}$ is chosen from linear and branched, saturated and unsaturated, $C_1$–$C_6$ hydrocarbon-based radicals.

In one embodiment, the $R_{15}$ alkyl radicals may be linear and branched and further, for example, linear.

For example, $R_{15}$ may be chosen from methyl, ethyl, hydroxyethyl and dihydroxypropyl radicals and further for example from methyl and ethyl radicals.

The sum x+y+z may for example range from 1 to 10.

When $R_{16}$ is chosen from linear and branched, saturated and unsaturated, $C_1$–$C_{22}$ hydrocarbon-based radicals, $R_{16}$ may be long and comprise from 12 to 22 carbon atoms, or short and comprise from 1 to 3 carbon atoms.

When $R_{18}$ is chosen from linear and branched, saturated and unsaturated, $C_1$–$C_6$ hydrocarbon-based radicals, $R_{18}$ may for example comprise from 1 to 3 carbon atoms.

$R_{17}$, $R_{19}$ and $R_{21}$, which may be identical or different, can, for example, be independently chosen from linear and branched, saturated and unsaturated $C_{11}$–$C_{21}$ hydrocarbon-based radicals, and for example from linear and branched, saturated and unsaturated, $C_{11}$–$C_{21}$, alkyl and alkenyl radicals.

x and z, which may be identical or different, can for example independently be chosen from 0 or 1.

y for example may be equal to 1.

n, p and r, which may be identical or different, can for example be independently chosen from 2 and 3 and in one embodiment equal to 2.

The anion for example can be chosen from halides (chloride, bromide, and iodide) and alkyl sulfates, such as methyl sulfate. However, methanesulfonate, phosphate, nitrate, tosylate, anions derived from organic acids, such as acetate and lactate, and any other anions compatible with the ammonium comprising an ester function, may be used.

As a further example, the anion $X^-$ can be chosen from chloride and methyl sulfate.

Further examples of ammonium salts of formula (VII) are those in which:

$R_{15}$ is chosen from methyl and ethyl radicals,
x and y are equal to 1;
z is equal to 0 or 1;
n, p and r are equal to 2;
$R_{16}$ is chosen from:
  acyl radicals

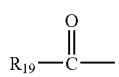

wherein $R_{19}$ is defined below,
  methyl, ethyl and $C_{14}$–$C_{22}$ hydrocarbon-based radicals, and
  a hydrogen atom;
$R_{18}$ is chosen from:
  acyl radicals

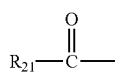

wherein $R_{21}$ is defined below,
  a hydrogen atom;
$R_{17}$, $R_{19}$ and $R_{21}$, which may be identical or different, are independently chosen from linear and branched, saturated and unsaturated, $C_{13}$–$C_{17}$ hydrocarbon-based radicals, such as from linear and branched, saturated and unsaturated $C_{13}$–$C_{17}$ alkyl and alkenyl radicals.

The hydrocarbon-based radicals can for example be linear.

Representative compounds of formula (VII) are chosen from diacyloxyethyl-dimethylammonium, diacyloxyethyl-hydroxyethylmethylammonium, monoacyloxyethyidihydroxyethylmethylammonium, triacyloxyethylmethylammonium and monoacyloxyethylhydroxyethyldimethylammonium salts (for example chloride and methyl sulfate). The acyl radicals can for example comprise from 14 to 18 carbon atoms and can for example be obtained from plant oils, such as palm oil and sunflower oil. When the compound comprises several acyl radicals, these radicals, which may be independently chosen, may independently be identical or different.

These products are obtained, for example, by direct esterification of compounds chosen from triethanolamine, triisopropanolamine, alkyldiethanolamines and alkyldiisopropanolamines, which are optionally oxyalkylenated, with fatty acids or with fatty acid mixtures of plant or animal origin, and by transesterification of the methyl esters thereof. This esterification is followed by a quaternization using an alkylating agent such as alkyl halides (such ad methyl and ethyl halides), dialkyl sulfates (for example dimethyl and diethyl sulfates), methyl methanesulfonate, methyl para-toluenesulfonate, glycol chlorohydrin and glycerol chlorohydrin.

Such compounds are sold, for example, under the names Dehyquart by the company Henkel, Stepanquat by the company Stepan, Noxamium by the company Ceca and Rewoquat WE 18 by the company Rewo-Witco.

It is also possible to use the ammonium salts comprising at least one ester function, described in patents U.S. Pat. No. 4,874,554 and U.S. Pat. No. 4,137,180, the disclosures of which are incorporated by reference herein.

Representative quaternary ammonium salts of formula (IV) include tetraalkylammonium chlorides such as, for example, dialkyldimethylammonium chlorides and alkyltrimethylammonium chlorides, in which the alkyl radical comprises from 12 to 22 carbon atoms, for example behenyltrimethylammonium chloride, distearyldimethylammonium chloride, cetyltrimethylammonium chloride, and benzyidimethylstearylammonium chloride, and, stearamidopropyldimethyl(myristyl acetate)ammonium chloride sold under the name "Cepharyl 70" by the company Van Dyk.

According to the invention, the at least one cationic surfactant can for example be present in an amount ranging from 0.1% to 20% by weight relative to the total weight of the final composition, such as from 0.1% to 10%, from 0.5% to 7%, and further such as from 1% to 5% by weight relative to the total weight of the final composition.

The composition of the invention can also comprise at least one additive chosen from fragrances, nacreous agents, preserving agents, silicone sunscreens, non-silicone sunscreens, vitamins, provitamins, amphoteric, anionic and nonionic polymers, proteins, protein hydrolysates, 18-methyleicosanoic acid, hydroxy acids, panthenol, volatile and non-volatile, cyclic and linear and crosslinked, modified and non-modified silicones, ceramides, pseudoceramides, plant, animal, mineral and synthetic oils and any other additive conventionally used in cosmetics which does not substantially adversely affect the properties of the compositions according to the invention.

Generally, these additives are present in the composition according to the invention in amounts, for example, ranging from 0 to 20% by weight relative to the total weight of the composition. The precise amount of each additive is readily determined by those skilled in the art depending on its nature and its function.

The compositions in accordance with the invention can also be used for washing or treating at least one keratin material chosen from hair, skin, eyelashes, eyebrows, nails, lips, scalp, and hair.

The compositions according to the invention can also be a detergent composition chosen from shampoos, shower gels, bubble baths and make-up-removing products. In this embodiment of the invention, the compositions comprise a washing base, which is generally aqueous.

At least one surfactant forms the washing base and can be chosen from anionic, amphoteric, nonionic and cationic surfactants, such as those defined above.

The quantity and quality of the washing base are sufficient to give the final composition at least one of the following qualities, satisfactory foaming power and satisfactory detergent power.

According to the invention, the washing base can be present for example in an amount ranging from 4% to 50% by weight, such as from 6% to 35% by weight and even further such as from 8% to 25% by weight, relative to the total weight of the final composition.

Another subject of the invention is also a process for treating keratin materials such as the skin and the hair, comprising applying a cosmetic composition as defined above to the keratin materials and optionally rinsing it out with water.

Thus, this process according to the invention allows maintenance of the hairstyle and treatment of, care of, washing of or removal of make-up from the skin, the hair or any other keratin material.

The compositions of the invention can for example be in forms chosen from rinse-out conditioners and leave-in conditioners; permanent-waving, straightening, dyeing and bleaching compositions; rinse-out compositions to be applied before a procedure chosen from dyeing, bleaching, permanent-waving and straightening the hair; rinse-out compositions to be applied after a procedure chosen from dyeing, bleaching, permanent-waving and straightening the hair; and rinse-out compositions to be applied between the two steps of a procedure chosen from permanent-waving and straightening the hair.

The compositions according to the invention can also be in a form chosen from aqueous and aqueous-alcoholic lotions for a care chosen from skin care and hair care.

The cosmetic compositions according to the invention can be in a form chosen from gels, milks, creams, emulsions, thickened lotions and mousses and can be used for treating at least one keratin material chosen from skin, nails, eyelashes, lips, and hair.

The compositions can be packaged in various forms chosen from vaporizers, pump-dispenser bottles and aerosol containers in order to ensure application of the composition in vaporized form or in the form of a mousse. Such packaging forms are indicated, for example, when it is desired to obtain a spray, a lacquer or a mousse for treating the hair.

In all of the text hereinabove and hereinbelow, the percentages expressed are on a weight basis.

The invention will now be illustrated more fully with the aid of the examples which follow, which should not be considered as limiting it to the embodiments described. In the examples, AM means active material.

EXAMPLE 1

A conditioner in accordance with the invention, having the following composition, was prepared:

| | |
|---|---:|
| Cationic emulsion containing 67% AM of copolymer of polydimethylsiloxane containing a,ω-vinyl groups/polydimethyl-siloxane containing a,ω-hydrogeno groups (DC-1997 from Dow Corning) | 4 gAM |
| SDMI/polyethylene glycol/alkyl (methyl/C18) endings copolymer at a concentration of 15% in a maltodextrin/water matrix (Aculyn 46 from Rohm & Haas) | 0.6 gAM |
| crosslinked ethyltrimethylammonium methacrylate chloride homopolymer as a reverse emulsion at a concentration of 50% in mineral oil (Salcare SC 95 from Ciba Geigy) | 0.55 gAM |
| Mixture of cetyl alcohol and of stearyl alcohol (50/50 by weight) | 2 g |
| Fragrance, preserving agents | qs |
| Water | qs 100 g |

This composition is applied to washed and dried hair. It is left to stand on the hair for 2 minutes and is then rinsed off thoroughly with water.

Hair treated with this conditioner is soft, smooth and disentangles easily.

What is claimed is:

1. A cosmetic composition comprising, in a cosmetically acceptable medium, at least one associative thickener and at least one aqueous emulsion comprising at least one silicone copolymer with a dynamic viscosity ranging from $1 \times 10^6$ to $100 \times 10^6$ cP, resulting from the addition reaction, in the presence of a catalyst, of at least:

(a) one polysiloxane of formula (I):

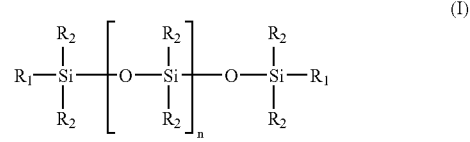

in which:
R$_1$, which may be identical or different, are independently chosen from groups that can react by chain addition reaction,
R$_2$ in formula (I), which may be identical or different, are independently chosen from alkyl, alkenyl, cycloalkyl, aryl, hydroxyl, and alkylaryl groups, and can optionally further comprise functional groups,
n is an integer wherein the polysiloxane of formula (I) has a kinematic viscosity ranging from 1 to $1 \times 10^6$ mm$^2$/s; and (b) at least one silicone compound comprising at least one and not more than two groups capable of reacting with the groups R$_1$ of the polysiloxane (a), wherein:
at least one of the compounds of type (a) and (b) comprises an aliphatic group comprising an ethylenic unsaturation;
wherein said at least one associative thickener is chosen from nonionic amphiphilic polymers chosen from
(1) celluloses modified with at least one group comprising at least one fatty chain; and
(2) polyether urethanes comprising at least one fatty chain,
wherein said at least one fatty chain comprises from 8 to 30 carbon atoms.

2. A composition according to claim 1, wherein R$_1$ is chosen from a hydrogen atom and aliphatic groups comprising an ethylenic unsaturation.

3. A composition according to claim 2, wherein the aliphatic groups comprising an ethylenic unsaturation are chosen from vinyl, allyl and hexenyl groups.

4. A composition according to claim 1, wherein the groups $R_2$ are chosen from hydroxyl groups; alkyl groups comprising from 1 to 20 carbon atoms; cycloalkyl groups comprising from 5 to 6 carbon atoms; phenyl groups; alkylaryl groups comprising from 7 to 20 carbon atoms; and can optionally further comprise functional groups chosen from ethers, amines, carboxyls, hydroxyls, thiols, esters, sulfonates and sulfates.

5. A composition according to claim 1, wherein said alkenyl groups are chosen from alkenyl groups comprising from 2 to 10 carbon atoms.

6. A composition according to claim 1, wherein $R_2$ is a methyl group.

7. A composition according to claim 1, wherein n is an integer ranging from 5 to 5,000.

8. A composition according to claim 1, wherein the compound of type (b) is another polysiloxane of type (a) in which at least one and not more than two groups $R_1$ of the polysiloxane (b) can react with the groups $R_1$ of the polysiloxane (a).

9. A composition according to claim 1, wherein, in the presence of a hydrosilylation catalyst, the at least one silicone copolymer is obtained by addition reaction of at least:
(a) one α,ω-divinylpolydimethylsiloxane, and
(b) one α,ω-dihydrogenopolydimethylsiloxane.

10. A composition according to claim 9, wherein the hydrosilylation catalyst is a platinum catalyst.

11. A composition according to claim 1, wherein said aqueous emulsion of the at least one silicone copolymer has a silicone droplet or particle size ranging from 10 nm to 50 μm.

12. A composition according to claim 11, wherein said emulsion of the at least one silicone copolymer has a silicone droplet or particle size ranging from 0.3 μm to 20 μm.

13. A composition according to claim 1, wherein said aqueous emulsion of the at least one silicone copolymer represents from 0.5% to 15% by weight relative to the total weight of the composition.

14. A composition according to claim 1, wherein the at least one silicone copolymer is essentially non-crosslinked.

15. A composition according to claim 1, wherein the at least one silicone copolymer is present in an amount ranging from 0.05% to 10% by weight relative to the total weight of the composition.

16. A composition according to claim 15, wherein the at least one silicone copolymer is present in an amount ranging from 0.1% to 5% by weight relative to the total weight of the composition.

17. A composition according to claim 1 further comprising at least one cationic surfactant chosen from:
A) quaternary ammonium salts of formula (IV) below:

in which:
the radicals $R_1$, $R_2$, $R_3$, and $R_4$, which may be identical or different, are independently chosen from linear and branched aliphatic radicals comprising from 1 to 30 carbon atoms, and aromatic radicals, wherein the aliphatic radicals optionally comprise hetero atoms, and $X^-$ is an anion chosen from the group of halides, phosphates, anions derived from organic acids, ($C_2$–$C_6$)alkyl sulfates, alkyl sulfonates, and alkylaryl sulfonates;

B) quaternary ammonium salts of imidazolinium of formula (V) below:

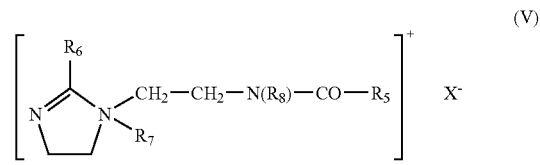

in which:
$R_5$ is chosen from alkenyl and alkyl radicals comprising from 8 to 30 carbon atoms,
$R_6$ is chosen from a hydrogen atom, $C_1$–$C_4$ alkyl radicals, and alkenyl and alkyl radicals comprising from 8 to 30 carbon atoms,
$R_7$ is chosen from $C_1$–$C_4$ alkyl radicals,
$R_8$ is chosen from a hydrogen atom and $C_1$–$C_4$ alkyl radicals, and
$X^-$ is an anion chosen from halides, phosphates, acetates, lactates, alkyl sulfates, alkyl sulfonates, and alkylaryl sulfonates;

C) diquaternary ammonium salts of formula (VI):

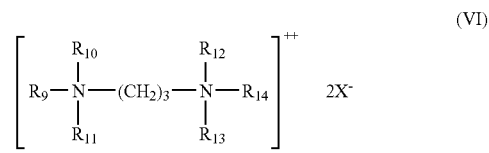

in which:
$R_9$ is chosen from aliphatic radicals comprising from 16 to 30 carbon atoms,
$R_{10}$, $R_{11}$, $R_{12}$, $R_{13}$ and $R_{14}$, which may be identical or different, are independently chosen from a hydrogen atom and alkyl radicals comprising from 1 to 4 carbon atoms, and
$X^-$ is an anion chosen from halides, acetates, phosphates, nitrates and methyl sulfates;

D) quaternary ammonium salts of formula (VII) below comprising at least one ester function:

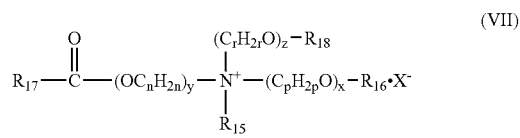

in which:
$R_{15}$ is chosen from $C_1$–$C_6$ alkyl radicals and $C_1$–$C_6$ hydroxyalkyl and $C_1$–$C_6$ dihydroxyalkyl radicals;
$R_{16}$ is chosen from:
acyl groups of the following formula:

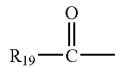

wherein $R_{19}$ is defined below,
linear and branched, saturated and unsaturated, $C_1$–$C_{22}$ hydrocarbon-based radicals, and
a hydrogen atom;
$R_{18}$ is chosen from:
acyl groups of the following formula:

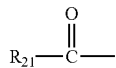

wherein $R_{21}$ is defined below,
linear and branched, saturated and unsaturated, $C_1$–$C_6$ hydrocarbon-based radicals, and
a hydrogen atom;
$R_{17}$, $R_{19}$ and $R_{21}$, which may be identical or different, are independently chosen from linear and branched, saturated and unsaturated, $C_7$–$C_{21}$ hydrocarbon-based radicals;
n, p and r, which may be identical or different, are independently integers ranging from 2 to 6;
y is an integer ranging from 1 to 10;
x and z, which may be identical or different, are independently integers ranging from 0 to 10; and
$X^-$ is chosen from simple and complex, organic and inorganic anions; and
provided that the sum x+y+z is from 1 to 15, and that when x is 0, then $R_{16}$ is chosen from linear and branched, saturated and unsaturated, $C_1$–$C_{22}$ hydrocarbon-based radicals, and that when z is 0, then $R_{18}$ is chosen from linear and branched, saturated and unsaturated, $C_1$–$C_6$ hydrocarbon-based radicals.

18. A composition according to claim 17, wherein said at least one cationic surfactant is chosen from:

A) quaternary ammonium salts of formula (IV) below:

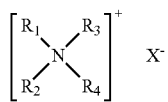 (IV)

wherein:
$X^-$ is an anion chosen from halides, ($C_2$–$C_6$)alkyl sulfates, phosphates, alkyl and alkylaryl sulfonates, and anions derived from organic acids, and
i) the radicals $R_1$, $R_2$, and $R_3$, which may be identical or different, are independently chosen from linear and branched aliphatic radicals comprising from 1 to 4 carbon atoms, optionally comprising hetero atoms, and aromatic radicals, and
$R_4$ is chosen from linear and branched alkyl radicals comprising from 16 to 30 carbon atoms;
ii) the radicals $R_1$ and $R_2$, which may be identical or different, are independently chosen from linear and branched aliphatic radicals comprising from 1 to 4 carbon atoms, optionally comprising hetero atoms, and aromatic radicals, and $R_3$ and $R_4$, which may be identical or different, are independently chosen from linear and branched alkyl radicals comprising from 12 to 30 carbon atoms, wherein said radicals further comprise at least one function chosen from ester and amide functions.

19. A composition according to claim 17, wherein in said quaternary ammonium salts of formula (VII):
$R_{15}$ is chosen from methyl and ethyl radicals,
x and y are equal to 1;
z is equal to 0 or 1;
n, p and r are equal to 2;
$R_{16}$ is chosen from:
acyl radicals

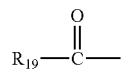

wherein $R_{19}$ is defined below,
methyl, ethyl and $C_{14}$–$C_{22}$ hydrocarbon-based radicals, and
a hydrogen atom;
$R_{18}$ is chosen from:
acyl radicals

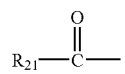

wherein $R_{21}$ is defined below,
a hydrogen atom; and
$R_{17}$, $R_{19}$ and $R_{21}$, which may be identical or different, are independently chosen from linear and branched, saturated and unsaturated, $C_{13}$–$C_{17}$ hydrocarbon-based radicals.

20. A composition according to claim 19, wherein $R_{17}$, $R_{19}$ and $R_{21}$ are chosen from linear and branched, saturated and unsaturated $C_{13}$–$C_{17}$ aliphatic radicals.

21. A composition according to claim 19, wherein the hydrocarbon-based radicals are chosen from linear hydrocarbon-based radicals.

22. A composition according to claim 17, wherein the compounds of formula (VII) are chosen from diacyloxyethlidimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts.

23. A composition according to claim 22, wherein said monoacyloxyethylhydroxyethyldimethylammonium salts are chosen from monoacyloxyethylhydroxyethyldimethylammonium chloride salts and monoacyloxyethylhydroxyethyldimethylammonium methyl sulfate salts.

24. A composition according to claim 19, wherein when $R_{16}$ and $R_{18}$ are chosen from acyl radicals, said acyl radicals are obtained from plant oils chosen from palm oil and sunflower oil.

25. A composition according to claim 17, wherein $X^-$ of said quaternary ammonium salts of formula (IV) is an anion chosen from chloride, bromide, iodide, methyl sulfate, acetate, and lactate.

26. A composition according to claim 17, wherein said aromatic radicals of said quaternary ammonium salts of formula (IV) are chosen from aryl and alkylaryl.

27. A composition according to claim 17, wherein said hetero atoms of said quaternary ammonium salts of formula (IV) are chosen from oxygen, nitrogen, sulfur and halogens.

28. A composition according to claim 18, wherein said aliphatic radicals of formula (IV)(ii) are chosen from alkyl, alkoxy, alkylamide, polyoxy($C_2$–$C_6$)alkylene, and hydroxyalkyl radicals comprising from 1 to 4 carbon atoms.

29. A composition according to claim 18, wherein said $R_3$ and $R_4$ of formula (IV)(ii) are chosen from ($C_{12}$–$C_{22}$) alkylamido($C_2$–$C_6$)alkyl and ($C_{12}$–$C_{22}$)alkylacetate radicals.

30. A composition according to claim 17, wherein said $R_5$ of formula (V) is chosen from radicals derived from tallow fatty acid.

31. A composition according to claim 17, wherein in said quaternary ammonium salts of imidazolinium of formula (V):
$R_5$ and $R_6$, which may be identical or different, are independently chosen from alkenyl and alkyl radicals comprising from 12 to 21 carbon atoms,
$R_7$ is methyl, and
$R_8$ is hydrogen.

32. A composition according to claim 31, wherein said $R_5$ and $R_6$, which may be identical or different, are independently chosen from radicals derived from tallow fatty acid.

33. A composition according to claim 17, wherein said diquaternary ammonium salts comprise propane tallow diammonium dichloride.

34. A composition according to claim 17, wherein said $R_{15}$ alkyl radicals of said quaternary ammonium salts of formula (VII) are chosen from linear and branched $C_1$–$C_6$ alkyl radicals.

35. A composition according to claim 34, wherein said $R_{15}$ radicals are linear radicals.

36. A composition according to claim 35, wherein said $R_{15}$ radicals are chosen from methyl, ethyl, hydroxyethyl and dihydroxypropyl.

37. A composition according to claim 36, wherein said $R_{15}$ radicals are chosen from methyl and ethyl.

38. A composition according to claim 17, wherein said sum of x+y+z of said quaternary ammonium salts of formula (VII) ranges from 1–10.

39. A composition according to claim 17, wherein said quaternary ammonium salts of formula (IV) are chosen from (a) compounds comprising at least two fatty aliphatic radicals comprising from 8 to 30 carbon atoms, (b) compounds comprising at least one fatty aliphatic radical comprising from 17 to 30 carbon atoms, and (c) compounds comprising at least one aromatic radical.

40. A composition according to claim 17, wherein said at least one cationic surfactant is chosen from behenyltrimethylammonium salts, stearamidopropyldimethyl(myristyl acetate)ammonium salts, Quaternium-27 and Quaternium-83.

41. A composition according to claim 17, wherein the at least one cationic surfactant is present in an amount ranging from 0.1% to 10% by weight relative to the total weight of the composition.

42. A composition according to claim 41, wherein the at least one cationic surfactant is present in an amount ranging from 0.5% to 7% by weight relative to the total weight of the composition.

43. A composition according to claim 42, wherein the at least one cationic surfactant is present in an amount ranging from 1% to 5% by weight relative to the total weight of the composition.

44. A composition according to claim 1 further comprising at least one surfactant chosen from anionic, nonionic, and amphoteric surfactants.

45. A composition according to claim 44, wherein the at least one surfactant chosen from anionic, nonionic, and amphoteric surfactants is present in an amount ranging from 0.1% to 60% by weight, relative to the total weight of the composition.

46. A composition according to claim 45, wherein the at least one surfactant chosen from anionic, nonionic, and amphoteric surfactants is present in an amount ranging from 3% to 40% by weight, relative to the total weight of the composition.

47. A composition according to claim 46, wherein the at least one surfactant chosen from anionic, nonionic, and amphoteric surfactants is present in an amount ranging from 5% to 30% by weight, relative to the total weight of the composition.

48. A composition according to claim 44, wherein the at least one surfactant chosen from anionic, nonionic, and amphoteric surfactants comprises at least one anionic surfactant salt chosen from alkyl sulfates, alkyl ether sulfates, alkylamidoether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates and N-acyltaurates.

49. A composition according to claim 44, wherein said at least one surfactant is chosen from anionic surfactants chosen from alkaline salts, sodium salts, ammonium salts, amine salts, amino alcohol salts and magnesium salts.

50. A composition according to claim 48, wherein said alkyl and acyl portions of radicals of said salts comprise 1 and from 8 to 24 carbon atoms, and said aryl portions of radicals of said salts are phenyl.

51. A composition according to claim 44, wherein said at least one surfactant is chosen from anionic surfactants chosen from fatty acid salts, acyl lactates wherein the acyl radical comprises 8 to 20 carbon atoms, and weakly anionic surfactants.

52. A composition according to claim 51, wherein said fatty acid salts are chosen from the salts of oleic acid, ricinoleic acid, palmitic acid, stearic acid, coconut oil acid and hydrogenated coconut oil acid.

53. A composition according to claim 44, wherein said at least one surfactant is chosen from anionic surfactants chosen from alkyl-D-galactosiduronic acids and their salts, polyoxyalkylenated ($C_6$–$C_{24}$) alkyl ether carboxylic acids and their salts, polyoxyalkylenated ($C_6$–$C_{24}$) alkylaryl ether carboxylic acids and their salts, and polyoxyalkylenated ($C_6$–$C_{24}$) alkylamido ether carboxylic acids and their salts.

54. A composition according to claim 51, wherein said weakly anionic surfactants comprise from 2 to 50 ethylene oxide groups.

55. A composition according to claim 48, wherein said at least one anionic surfactant salt is chosen from alkyl sulfates and alkyl ether sulfates.

56. A composition according to claim 44, wherein said at least one surfactant is chosen from nonionic surfactants chosen from polyethoxylated, polypropoxylated and polyglycerolated fatty acids, alkylphenols, α-diols and alcohols having a fatty aliphatic chain comprising 8 to 18 carbon atoms, wherein the number of ethylene oxide and propylene oxide groups ranges from 2 to 50 and the number of glycerol groups ranges from 2 to 30, copolymers of ethylene oxide and of propylene oxide, condensates of ethylene oxide and of propylene oxide with fatty alcohols, polyethoxylated fatty amides comprising from 2 to 30 mol of ethylene oxide, polyglycerolated fatty amides comprising on average 1 to 5 glycerol groups, polyethoxylated fatty amines comprising from 2 to mol of ethylene oxide, oxyethylenated fatty acid esters of sorbitan comprising from 2 to 30 mol of ethylene oxide, fatty acid esters of sucrose, fatty acid esters of polyethylene glycol, alkylpolyglycosides, N-alkylglucamine derivatives, and amine oxides.

57. A composition according to claim 56, wherein said polyglycerolated fatty amides comprise on average 1.5 to 4 glycerol groups.

58. A composition according to claim 56, wherein said amine oxides are chosen from ($C_{10}$–$C_{14}$)alkylamine oxides and N-acylaminopropylmorpholine oxides.

59. A composition according to claim 56, wherein said nonionic surfactants are chosen from alkylpolyglycosides.

60. A composition according to claim 44, wherein said at least one surfactant is chosen from amphoteric surfactants chosen from aliphatic secondary and tertiary amine derivatives wherein the aliphatic radical is chosen from linear and branched chain radicals comprising 8 to 22 carbon atoms and comprising at least one water-soluble anionic group, ($C_8$–$C_{20}$)alkylbetaines, sulfobetaines, ($C_8$–$C_{20}$)alkylamido($C_1$–$C_6$)alkylbetaines, and ($C_8$–$C_{20}$)alkylamido($C_1$–$C_6$)alkylsulfobetaines.

61. A composition according to claim 60, wherein said at least one water-soluble anionic group is chosen from carboxylates, sulfonates, sulfates, phosphates and phosphonates.

62. A composition according to claim 60, wherein said amine derivatives are chosen from the compounds:

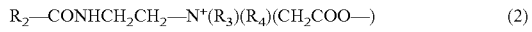

in which:
R$_2$ is chosen from alkyl radicals derived from an acid R$_2$—COOH present in hydrolysed coconut oil, heptyl, nonyl and undecyl radicals,
R$_3$ is chosen from β-hydroxyethyl groups, and
R$_4$ is chosen from carboxymethyl groups; and

in which:
(B) is —CH$_2$CH$_2$OX', with X' chosen from a —CH$_2$CH$_2$—COOH group and a hydrogen atom,
(C) is —(CH$_2$)$_z$—Y', with z=1 or 2, and with Y' chosen from —COOH and —CH$_2$—CHOH—SO$_3$H radicals,
R$_5$ is chosen from alkyl radicals and unsaturated C$_{17}$ radicals.

63. A composition according to claim 62, wherein said alkyl radicals R$_5$ are chosen from (a) alkyl radicals of an acid R$_5$—COOH present in oils chosen from coconut oil and hydrolysed linseed oil, and (b) C$_{17}$ alkyl radicals and the iso forms.

64. A composition according to claim 62, wherein said alkyl radicals of said R$_5$ are chosen from alkyl radicals chosen from C$_7$, C$_9$, C$_{11}$ and C$_{13}$ alkyl radicals.

65. A composition according to claim 44, wherein said at least one surfactant is chosen from at least two surfactants of different types.

66. A composition according to claim 65, wherein said at least two surfactants of different types are chosen from (a) more than one anionic surfactant, (b) at least one anionic surfactant and at least one amphoteric surfactant, and (c) at least one anionic surfactant and and at least one nonionic surfactant.

67. A composition according to claim 44, wherein said at least one surfactant is chosen from anionic surfactants chosen from (C$_{12}$–C$_{14}$)alkyl sulfates of sodium, of triethanolamine and of ammonium, (C$_{12}$–C$_{14}$)alkyl ether sulfates of sodium, of triethanolamine and of ammonium, oxyethylenated with 2.2 mol of ethylene oxide, sodium cocoyl isethionate, and sodium (C$_{14}$–C$_{16}$)-α-olefin sulfonate, and from an amphoteric surfactant chosen from either:
amine derivatives comprising disodium cocoamphodipropionate and sodium cocoamphopropionate, or
amphoteric surfactants of zwitterionic type.

68. A composition according to claim 67, wherein said amphoteric surfactants of zwitterionic type are chosen from alkylbetaines.

69. A composition according to claim 68, wherein said alkylbetaines are chosen from cocobetaine.

70. A composition according to claim 1 further comprising at least one additive chosen from fragrances, nacreous agents, preserving agents, silicone sunscreens, non-silicone sunscreens, vitamins, provitamins, amphoteric, anionic and nonionic polymers, proteins, protein hydrolysates, 18-methyleicosanoic acid, hydroxy acids, panthenol, volatile and non-volatile, cyclic and linear and crosslinked, modified and non-modified silicones, ceramides, pseudoceramides, and plant, animal, mineral and synthetic oils.

71. A composition according to claim 70, wherein said at least one additive is present in an amount ranging from 0 to 20% by weight relative to the total weight of the composition.

72. A rinse-out conditioner, a leave-in conditioner, a composition for permanent-waving the hair, a composition for straightening the hair, a composition for dyeing the hair, a composition for bleaching the hair, a rinse-out composition to be applied before a procedure chosen from dyeing, bleaching, permanent-waving and straightening the hair, a rinse-out composition to be applied after a procedure chosen from dyeing, bleaching, permanent-waving and straightening the hair, a rinse-out composition to be applied between the two steps of a permanent-waving operation, a rinse-out composition to be applied between the two steps of a hair-straightening operation, a washing composition for the body, an aqueous lotion, an aqueous-alcoholic lotion, a gel, a milk, a cream, an emulsion, a thickened lotion, a mousse, or a detergent composition comprising a washing base comprising, in a cosmetically acceptable medium, at least one associative thickener and at least one aqueous emulsion comprising at least one silicone copolymer with a dynamic viscosity ranging from 1×10$^6$ to 100×10$^6$ cP, resulting from the addition reaction, in the presence of a catalyst, of at least:
(a) one polysiloxane of formula (I):

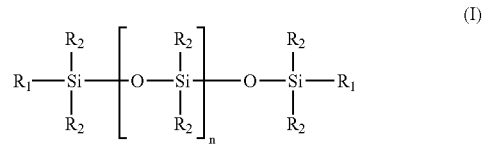

in which:
R$_1$, which may be identical or different, are independently chosen from groups that can react by chain addition reaction,
R$_2$ in formula (I), which may be identical or different, are independently chosen from alkyl, alkenyl, cycloalkyl, aryl, hydroxyl, and alkylaryl groups, and can optionally further comprise functional groups, n is an integer wherein the polysiloxane of formula (I) has a kinematic viscosity ranging from 1 to $1 \times 10^6$ mm$^2$/s; and (b) at least one silicone compound comprising at least one and not more than two groups capable of reacting with the groups R$_1$ of the polysiloxane (a), wherein:

at least one of the compounds of type (a) and (b) comprises an aliphatic group comprising an ethylenic unsaturation;

wherein said at least one associative thickener is chosen from nonionic amphiphilic polymers chosen from (1) celluloses modified with at least one group comprising at least one fatty chain; and (2) polyether urethanes comprising at least one fatty chain, wherein said at least one fatty chain comprises from 8 to 30 carbon atoms.

73. An aqueous or aqueous-alcoholic lotion according to claim 72, said lotion being suitable for skin care or for hair care.

74. A gel, a milk, a cream, an emulsion, a thickened lotion or a mousse according to claim 72, wherein said gel, milk, cream, emulsion, thickened lotion or mousse is suitable to be applied to at least one keratin material chosen from skin, nails, eyelashes, lips and hair.

75. A detergent composition comprising a washing base according to claim 72, wherein said composition is chosen from shampoos, shower gels, bubble baths and make-up-removing products.

76. A detergent composition comprising a washing base according to claim 72, wherein said washing base comprises at least one surfactant chosen from anionic, amphoteric, nonionic and cationic surfactants.

77. A detergent composition according to claim 76, wherein said at least one surfactant is present in an amount effective to provide satisfactory foaming power and satisfactory detergent power.

78. A detergent composition comprising a washing base according to claim 76, wherein said washing base is present in an amount ranging from 4% to 50% by weight, relative to the total weight of the final composition.

79. A detergent composition comprising a washing base according to claim 78, wherein said washing base is present in an amount ranging from 6% to 35% by weight, relative to the total weight of the final composition.

80. A detergent composition comprising a washing base according to claim 79, wherein said washing base is present in an amount ranging from 8% to 25% by weight, relative to the total weight of the final composition.

81. A process of washing or caring for a keratin material comprising applying to said keratin material a composition comprising, in a cosmetically acceptable medium, at least one associative thickener and at least one aqueous emulsion comprising at least one silicone copolymer with a dynamic viscosity ranging from $1 \times 10^6$ to $100 \times 10^6$ cP, resulting from the addition reaction, in the presence of a catalyst, of at least:

(a) one polysiloxane of formula (I):

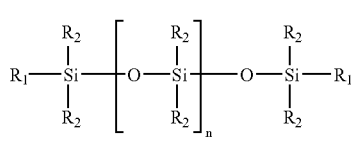

in which:

R$_1$, which may be identical or different, are independently chosen from groups that can react by chain addition reaction, R$_2$ in formula (I), which may be identical or different, are independently chosen from alkyl, alkenyl, cycloalkyl, aryl, hydroxyl, and alkylaryl groups, and can optionally further comprise functional groups, n is an integer wherein the polysiloxane of formula (I) has a kinematic viscosity ranging from 1 to $1 \times 10^6$ mm$^2$/s; and (b) at least one silicone compound comprising at least one and not more than two groups capable of reacting with the groups R$_1$ of the polysiloxane (a), wherein:

at least one of the compounds of type (a) and (b) comprises an aliphatic group comprising an ethylenic unsaturation;

wherein said at least one associative thickener is chosen from nonionic amphiphilic polymers chosen from (1) celluloses modified with at least one group comprising at least one fatty chain; and (2) polyether urethanes comprising at least one fatty chain, wherein said at least one fatty chain comprises from 8 to 30 carbon atoms.

82. A process for treating a keratin material comprising applying to said keratin material a composition comprising, in a cosmetically acceptable medium, at least one associative thickener and at least one aqueous emulsion comprising at least one silicone copolymer with a dynamic viscosity ranging from $1 \times 10^6$ to $100 \times 10^6$ cP, resulting from the addition reaction, in the presence of a catalyst, of at least:

(a) one polysiloxane of formula (I):

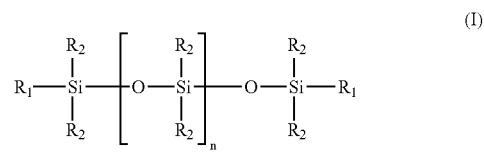

in which:

R$_1$, which may be identical or different, are independently chosen from groups that can react by chain addition reaction, R$_2$ in formula (I), which may be identical or different, are independently chosen from alkyl, alkenyl, cycloalkyl, aryl, hydroxyl, and alkylaryl groups, and can optionally further comprise functional groups, n is an integer wherein the polysiloxane of formula (I) has a kinematic viscosity ranging from 1 to $1 \times 10^6$ mm$^2$/s; and (b) at least one silicone compound comprising at least one and not more than two groups capable of reacting with the groups R$_1$ of the polysiloxane (a), wherein:

at least one of the compounds of type (a) and (b) comprises an aliphatic group comprising an ethylenic unsaturation;

wherein said at least one associative thickener is chosen from nonionic amphiphilic polymers chosen from (1) celluloses modified with at least one group comprising at least one fatty chain; and (2) polyether urethanes comprising at least one fatty chain, wherein said at least one fatty chain comprises from 8 to 30 carbon atoms; and optionally rinsing said composition out with water.

83. A process for washing or treating a keratin material according to claim 82, wherein said keratin material is chosen from hair, skin, eyelashes, eyebrows, nails, lips and scalp.

84. A process for manufacturing a cosmetic product comprising including in said product at least one associative thickener and at least one aqueous emulsion comprising at least one silicone copolymer with a dynamic viscosity ranging from $1 \times 10^6$ to $100 \times 10^6$ cP, resulting from the addition reaction, in the presence of a catalyst, of at least:

(a) one polysiloxane of formula (I):

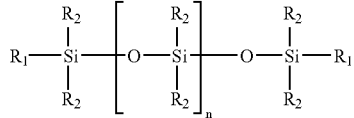

(I)

in which:

$R_1$ which may be identical or different, are independently chosen from groups that can react by chain addition reaction, $R_2$ in formula (I), which may be identical or different, are independently chosen from alkyl, alkenyl, cycloalkyl, aryl, hydroxyl, and alkylaryl groups, and can optionally further comprise functional groups, n is an integer wherein the polysiloxane of formula (I) has a kinematic viscosity ranging from 1 to $1 \times 10^6$ mm$^2$/s; and (b) at least one silicone compound comprising at least one and not more than two groups capable of reacting with the groups $R_1$ of the polysiloxane (a), wherein:

at least one of the compounds of type (a) and (b) comprises an aliphatic group comprising an ethylenic unsaturation;

wherein said at least one associative thickener is chosen from nonionic amphiphilic polymers chosen from (1) celluloses modified with at least one group comprising at least one fatty chain; and (2) polyether urethanes comprising at least one fatty chain, wherein said at least one fatty chain comprises from 8 to 30 carbon atoms.

85. A composition according to claim 1, wherein said polyether urethanes comprising at least one fatty chain are chosen from polyether urethanes comprising at least one fatty chain comprising at least one group chosen from $C_8$–$C_{30}$ alkyl groups and $C_8$–$C_{30}$ alkenyl groups.

86. A composition according to claim 1, wherein said at least one associative thickener is present in an amount ranging from 0.001% to 20% by weight relative to the total weight of said composition.

87. A composition according to claim 86, wherein said at least one associative thickener is present in an amount ranging from 0.01% to 10% by weight relative to the total weight of said composition.

* * * * *

UNITED STATES PATENT AND TRADEMARK OFFICE
CERTIFICATE OF CORRECTION

| | | |
|---|---|---|
| PATENT NO. | : 7,186,406 B2 | Page 1 of 1 |
| APPLICATION NO. | : 10/195021 | |
| DATED | : March 6, 2007 | |
| INVENTOR(S) | : Sandrine Decoster et al. | |

It is certified that error appears in the above-identified patent and that said Letters Patent is hereby corrected as shown below:

Claim 17, column 18, lines 56-60

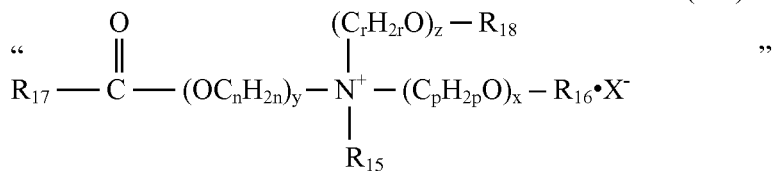

should read

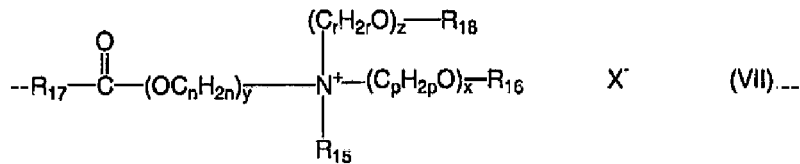

Claim 22, column 20, lines 47-48, "diacyloxyethlidimethylammonium," should read --diacyloxyethyldimethylammonium,--.

Claim 56, column 23, line 6, "2 to mol" should read --2 to 30 mol--.

Claim 84, column 27, line 22, "$R_1$ which" should read --$R_1$, which--.

Signed and Sealed this

Twelfth Day of June, 2007

JON W. DUDAS
*Director of the United States Patent and Trademark Office*